(12) United States Patent
Shah et al.

(10) Patent No.: US 11,147,608 B2
(45) Date of Patent: Oct. 19, 2021

(54) COMPUTERIZED ELECTRICAL SIGNAL GENERATOR

(71) Applicants: BAYLIS MEDICAL COMPANY INC., Mississauga (CA); AVENT, INC., Alpharetta, GA (US)

(72) Inventors: Krishan Shah, Mississauga (CA); Frank Headley Baylis, Beaconsfield (CA)

(73) Assignees: BAYLIS MEDICAL COMPANY INC., Montreal (CA); AVENT INC., Alpharetta, GA (US)

( * ) Notice: Subject to any disclaimer, the term of this patent is extended or adjusted under 35 U.S.C. 154(b) by 262 days.

(21) Appl. No.: 16/175,534

(22) Filed: Oct. 30, 2018

(65) Prior Publication Data

US 2019/0059977 A1  Feb. 28, 2019

Related U.S. Application Data

(63) Continuation of application No. 14/676,169, filed on Apr. 1, 2015, now abandoned, which is a continuation of application No. 11/840,732, filed on Aug. 17, 2007, now abandoned, which is a continuation of application No. 10/122,413, filed on Apr. 16, 2002, now Pat. No. 7,258,688.

(51) Int. Cl.
| | |
|---|---|
| A61B 18/12 | (2006.01) |
| A61B 90/98 | (2016.01) |
| A61B 18/00 | (2006.01) |

(52) U.S. Cl.
CPC .......... *A61B 18/1206* (2013.01); *A61B 90/98* (2016.02); *A61B 2018/00702* (2013.01); *A61B 2018/00791* (2013.01); *A61B 2018/00875* (2013.01); *A61B 2018/00988* (2013.01)

(58) Field of Classification Search
CPC ...... A61B 18/1206; A61B 2018/00702; A61B 2018/00791; A61B 2018/00875; A61B 2018/00988; A61B 90/98
See application file for complete search history.

(56) References Cited

U.S. PATENT DOCUMENTS

| 4,580,557 A | * | 4/1986 | Hertzmann | ............ A61B 18/20 |
| | | | | 219/121.61 |
| 5,233,515 A | | 8/1993 | Cosman | |

(Continued)

FOREIGN PATENT DOCUMENTS

| WO | 98/38913 | 9/1998 |
|---|---|---|
| WO | 99/16350 | 4/1999 |

OTHER PUBLICATIONS

Boston Scientific EP Technologies, "EPT-1000 XP, Cardiac Ablation System", copyright 2000, 2 pages.

(Continued)

*Primary Examiner* — Michael F Peffley
(74) *Attorney, Agent, or Firm* — Jenna L. Wilson; Wilson Lue LLP (57) ABSTRACT

The invention relates to a medical probe signal generator. More particularly, it relates to a medical probe signal generator architecture. The present invention further relates to a system including a medical probe signal generator having an automatic probe type detector for detecting an identifier and at least one instrument cable comprising the identifier.

18 Claims, 7 Drawing Sheets

(56) References Cited

U.S. PATENT DOCUMENTS

| | | | |
|---|---|---|---|
| 5,383,874 A | | 1/1995 | Jackson et al. |
| 5,400,267 A | * | 3/1995 | Denen ................. H02J 3/00 |
| | | | 702/59 |
| 5,456,682 A | | 10/1995 | Edwards et al. |
| 5,484,400 A | | 1/1996 | Edwards et al. |
| 5,496,312 A | | 3/1996 | Klicek |
| 5,514,129 A | | 5/1996 | Smith |
| 5,540,683 A | * | 7/1996 | Ichikawa ............. A61B 18/12 |
| | | | 606/38 |
| 5,542,916 A | | 8/1996 | Hirsch et al. |
| 5,599,344 A | | 2/1997 | Paterson |
| 5,720,744 A | | 2/1998 | Eggleston et al. |
| 5,743,903 A | * | 4/1998 | Stern ................. A61B 18/00 |
| | | | 606/31 |
| 5,755,715 A | | 5/1998 | Stern et al. |
| 5,772,659 A | | 6/1998 | Becker |
| 5,813,404 A | | 9/1998 | Devlin et al. |
| D404,004 S | | 1/1999 | Chen et al. |
| 5,865,788 A | | 2/1999 | Edwards et al. |
| 5,871,481 A | | 2/1999 | Kannenberg et al. |
| D411,004 S | | 6/1999 | Muller et al. |
| D411,622 S | | 6/1999 | Hall |
| 5,916,163 A | | 6/1999 | Panescu et al. |
| 5,957,922 A | | 9/1999 | Imran |
| 5,983,141 A | | 11/1999 | Sluijter et al. |
| 6,033,399 A | | 3/2000 | Gines |
| 6,067,475 A | | 5/2000 | Graves |
| 6,093,186 A | | 6/2000 | Goble |
| 6,102,907 A | | 8/2000 | Smethers et al. |
| 6,122,551 A | | 9/2000 | Rudie |
| 6,161,048 A | | 12/2000 | Sluijter et al. |
| 6,162,217 A | | 12/2000 | Kannenberg et al. |
| 6,165,169 A | * | 12/2000 | Panescu ............. A61B 18/1492 |
| | | | 606/1 |
| 6,193,713 B1 | | 2/2001 | Geistert |
| 6,203,541 B1 | | 3/2001 | Keppel |
| 6,210,403 B1 | | 4/2001 | Klicek |
| 6,217,574 B1 | | 4/2001 | Webster |
| 6,228,079 B1 | | 5/2001 | Koenig |
| 6,228,080 B1 | | 5/2001 | Gines |
| 6,231,569 B1 | | 5/2001 | Bek |
| 6,251,106 B1 | | 6/2001 | Becker et al. |
| 6,280,441 B1 | | 8/2001 | Ryan |
| 6,293,941 B1 | | 9/2001 | Strul et al. |
| 6,293,943 B1 | | 9/2001 | Panescu et al. |
| 6,309,386 B1 | | 10/2001 | Bek |
| 6,312,391 B1 | | 11/2001 | Ramadhyani |
| 6,387,092 B1 | | 5/2002 | Burnside et al. |
| 6,464,689 B1 | * | 10/2002 | Qin ................... A61B 18/1485 |
| | | | 606/1 |
| 6,666,860 B1 | | 12/2003 | Takahashi |
| 6,733,495 B1 | | 5/2004 | Bek et al. |
| 6,783,523 B2 | | 8/2004 | Qin et al. |
| 6,827,713 B2 | * | 12/2004 | Bek .................. A61B 18/00 |
| | | | 606/1 |

OTHER PUBLICATIONS

Dr. Osypka Gmbh, "Electrophys. RF-Ablation", URL: http://www.osypka.de/English/Products/electrophys_ablation.html, printed from the Internet Nov. 30, 2001, copyright 2000, 1 page.

RDG Medical Products, URL: http://www.rdgmedical.com/products.htm, printed from the Internet Nov. 30, 2001, copyright 1999, 2 pages.

RDG Medical Product, "The NeuroTherm JK3 Lesion Generator", URL: http://www.rdgmedical.com/prod01.htm, printed from the Internet Nov. 30, 2001, copyright 1999, 5 pages.

Somnus Medical Technologies, Inc., "Model S2 Radiofrequency Control Unit", URL: http://www.somnoplasty.com/MDTrack/Introduction/modelS2.html, copyright 1999, 5 pages.

Somnus Medical Technologies, Inc., 510(k) Summary of Safety and Effectiveness, Model S2 Electrosurgical Generator May 16, 2000, #K001438, 2 pages.

Somnus Medical Technologies, Inc., Department of Health and Human Services re: K001438, Trade name: Somnus Modified Model S2 Electrosurgical Generator May 16, 2000 and Indications for Use, 3 pages.

VidaMed Products, "VidaMed's TUNA System", URL: http://www.vidamed.com/products.htm, published at least as early as Apr. 10, 2001, 5 pages.

Urologix, "About the Targis System", URL: http://www.urologix.com/html/abouttarsys.htm, published at least as early as Apr. 10, 2001, 4 pages.

Urologix, "Targis Technology", URL: http://www.urologix.com/html/technology.htm, published at least as early as Apr. 10, 2001, 3 pages.

Urologix, "About The Prostatron System", URL: http://www.urologix.com/html/prostatron.htm, printed from the Internet Apr. 10, 2001, 5 pages.

Direx, "Ablative Outpatient Prostatic Therapy Turapy XL", URL: http://www.direx.co.il/therm.html, published at least as early as Apr. 10, 2001, 2 pages.

Valleylab, "Force EZ™ Electrosurgical Generator", URL: http://www.valleylab.com/displayproduct.cfm?productid= 121&menu= product, printed from the Internet Nov. 30, 2001, copyright 2001, 1 page.

Valleylab, "Force FX™ Electrosurgical Generator", URL: http://www.valleylab.com/displayproduct.cfm?productid=122&menu= product, printed from the Internet Nov. 30, 2001, copyright 2001, 1 page.

Valleylab, "Force™ 1C Generator", URL: http://wv.'W.valleylab.com/displayproduct.c fm ?productid=124&menu=product, printed from the Internet Nov. 30, 2001, copyright 2001, 1 page.

Valleylab, "Force™ 2 Generator", URL: http://www.valleylab.com/displayproduct.cfm?productid= I 23&menu=product, printed from the Internet Nov. 30, 2001, copyright 2001, 1 page.

Ceramoptec GmbH, "Cerdias D—high absorption diode laser", published at least as early as 2002, 1 page.

Radionics, "REG-3C Lesion Generator System", URL: http://www.radionics.com/products/rf/rfg3df_top.shtml, published at least as early as Oct. 20, 2000, 1 page.

Diros Technology Inc., "OWL Radio Frequency System" brochure, published in 2000, 3 pages.

Boston Scientific Corporation, "Summary of Safety and Effectiveness Data". Premarket Approval for EPT-1000 XP Cardiac Ablation Controller, FDA, Aug. 25, 2003, 19 pages.

\* cited by examiner

COMPUTERIZED ELECTRICAL SIGNAL GENERATOR

CROSS REFERENCES TO RELATED APPLICATIONS

This application is a continuation of U.S. patent application Ser. No. 14/676,169, filed Apr. 1, 2015, now abandoned, which is a continuation of U.S. patent application Ser. No. 11/840,732, filed on Apr. 16, 2002, now abandoned, which was a continuation of U.S. patent application Ser. No. 10/122,413, filed Apr. 16, 2002, now U.S. Pat. No. 7,258,688, issued Aug. 21, 2007, the entireties of which are incorporated herein by reference.

FIELD OF THE INVENTION

The invention relates generally to an energy generator. More particularly, the invention relates to an apparatus for providing a controlled source of energy to an application tool, combining features that customize the utilization to a particular specialization.

BACKGROUND OF THE INVENTION

Electrical signal generators are used in a variety of medical applications. Examples include electrosurgery, tissue ablation, tissue perforation, neural stimulation, and neural lesioning. Neural lesion procedures using electrical current with a high frequency wave, typically in the radiofrequency (RF) spectrum, have been in use since the early 1950s. Among a variety of therapeutic purposes, the application of RF in the nervous system is commonly used in the interventional treatment of pain. The principle of this application is to intervene in the transmission of pain signals by altering a function of a nerve structure. This is accomplished by controlled generation of heat, or, non-thermal delivery of RF current using an electrode connected to the generator. Modern RF electrodes not only deliver current but also include temperature sensors that feedback information to the controller. And thus, in this situation the energy application tool is interchangeably referred to as a RF electrode and RF probe. One of the major advantages of using electrical current for interventional pain management is that by applying appropriate frequencies, the current can be used to stimulate nerves adjacent the electrode to differentiate pain fibers from other neural fibers and ensure the correct placement of the electrode prior to intervention.

Currently, in the field of interventional treatment of chronic pain the specialist commonly uses three modes of RF treatment including standard RF, pulsed RF and intradiscal lesioning. Each of these treatment modes is based on the application of continuous or pulsed radiofrequency electrical current to tissue or to an application tool. For some procedures, prior to applying radiofrequency energy, the target site is stimulated using stimulation modes to ensure correct placement of the RF delivery probe.

RF Lesioning Devices—Probes and Cannula

Probes are medical devices that are designed to act as patient/energy interfaces for radiofrequency generator systems. The RF energy applied is usually a 400 to 900 kHz waveform that can be used for a variety of purposes. In most radiofrequency generators, the 460-500 kHz waveform is delivered to the body using a probe and cannula system. A cannula is a hypodermic needle with an insulated shaft and a bare metal tip called an active tip. It is called an active tip because once the probe is inserted into the cannula and the RF is activated, the tip becomes the energy delivery mechanism. The electrical circuit required to deliver current and voltage is provided by a return electrode pad that is placed on a flat body part of the patient, such as his thigh. When the RF energy is activated at the machine, RF is delivered to the cells surrounding the active tip surface area. With energy application, the cells move faster and generate heat. As this heat increases, it is detected by the temperature measurement device that is located in the probe.

Therefore, the mono-polar probe serves two major functions, it is used for RF energy delivery to the cannula and temperature monitoring through a thermocouple effect. In some cases, the probes are not truly heating devices (i.e. resistive elements), but rather passive energy delivery systems.

Intradiscal Lesioning Devices Probes

Historically, intradiscal devices work on the principle described above or on a different principle. Still using RF energy (for example, at 460 kHz) these bi-polar probes are designed to be heating elements. There is a resistive element in the probe that generates heat. When this probe is placed in the body it radiates heat to the tissue that surrounds it. There is no need for a return electrode, but there is a need to measure the temperature and provide that information to the generator for a temperature control function.

Therefore, the bi-polar probe serves two major functions. It is used for delivery of heat energy to the tissue in the disc and for temperature monitoring through a temperature sensor.

A limitation of conventional signal generators is that they are built with switches and controls hardwired in a dedicated manner for the specific generator. The components are therefore securely connected to each other for a specific function with limited reliance on the operation of a central processing unit. This limits the ease of use and adaptability of the signal generator.

For example, at the time of purchasing new medical probes for a new technique, it is common to acquire, at the same time, a dedicated electrical signal generator. Consequently, there is a significant cost associated with purchasing, storing and maintaining dedicated electrical signal generators for a large variety of medical probes. Upgrading a hardwired electrical signal generator to accommodate a new medical probe is costly, if possible at all. It is very difficult to change the functions of the machine without changing the actual physical parts and without adding user input controls such as buttons, switches and dials. In the Pain Management field, for example, this is costly and inefficient because there are a growing number of procedures being developed for the treatment of pain. Furthermore, the addition of the new technique decreases the ease of use as additional user input controls or components are added to the existing system.

Another example of this limitation is that there is also a significant cost related to training personnel, both doctors and nurses, in the use of such signal generators. Especially since this training must be done for each new signal generator. Each signal generator has its own proprietary configuration and requirements for use. The nurse or doctor must set switches and controls to desired settings prior to use.

Currently, the generic signal generators are very complex to use and require extensive training of personnel who operate them. The flow of operations is not intuitive and there is no support for the user for troubleshooting. Furthermore, excessive control buttons and switches that are not always needed for every procedure complicate the user interface. The complexity and lack of operational information makes the use of the current generators time consuming, frustrating and costly for the physicians because of increased training required.

SUMMARY OF THE INVENTION

There is therefore a need for an apparatus for delivering a controlled source of energy to an application tool, combining features that customize the utilization to a particular specialization, thus allowing ease of use and safety. There is also a need for an apparatus for delivering a controlled source of energy to an application tool that has flexibility for quick and inexpensive upgrading.

Accordingly, an object of the invention is to provide an energy generator built on a software platform that flexibly allows for modifications of programmed energy delivery profiles and use with different application tools.

According to one broad aspect of the present invention, there is provided an energy delivery system for delivering energy to a patient's body via at least one medical instrument of a plurality of different medical instruments, the system comprising an energy generator comprising a detector associated with an electrical connector port of the generator for detecting an identifier from a plurality of identifiers, the generator adapted to enable functions relevant to the identifier upon detecting the identifier; and at least one instrument cable comprising one of the plurality of identifiers, the cable comprising a first electrical connector for connection to the connector port of the generator and a second electrical connector for connection to a connector of the at least one medical instrument.

BRIEF DESCRIPTION OF THE DRAWINGS

These and other features, aspects and advantages of the present invention will become better understood with regard to the following exemplary and nonlimiting embodiments illustrated in the accompanying drawings wherein.

DETAILED DESCRIPTION OF THE PREFERRED EMBODIMENT

While illustrated in the block diagrams (FIGS. 2 and 3) as ensembles of discrete components communicating with each other via distinct data signal connections, it will be understood by those skilled in the art that the embodiments described herein are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present embodiment.

The signal generator has the ability to control the output and therefore the treatment in real time using a classical control system. In this case, the control system incorporates temperature feedback to adjust the level of current and voltage supplied to the tissue. Input to the control system is provided from the tissue temperature measurements made by the probe.

Figure 1:
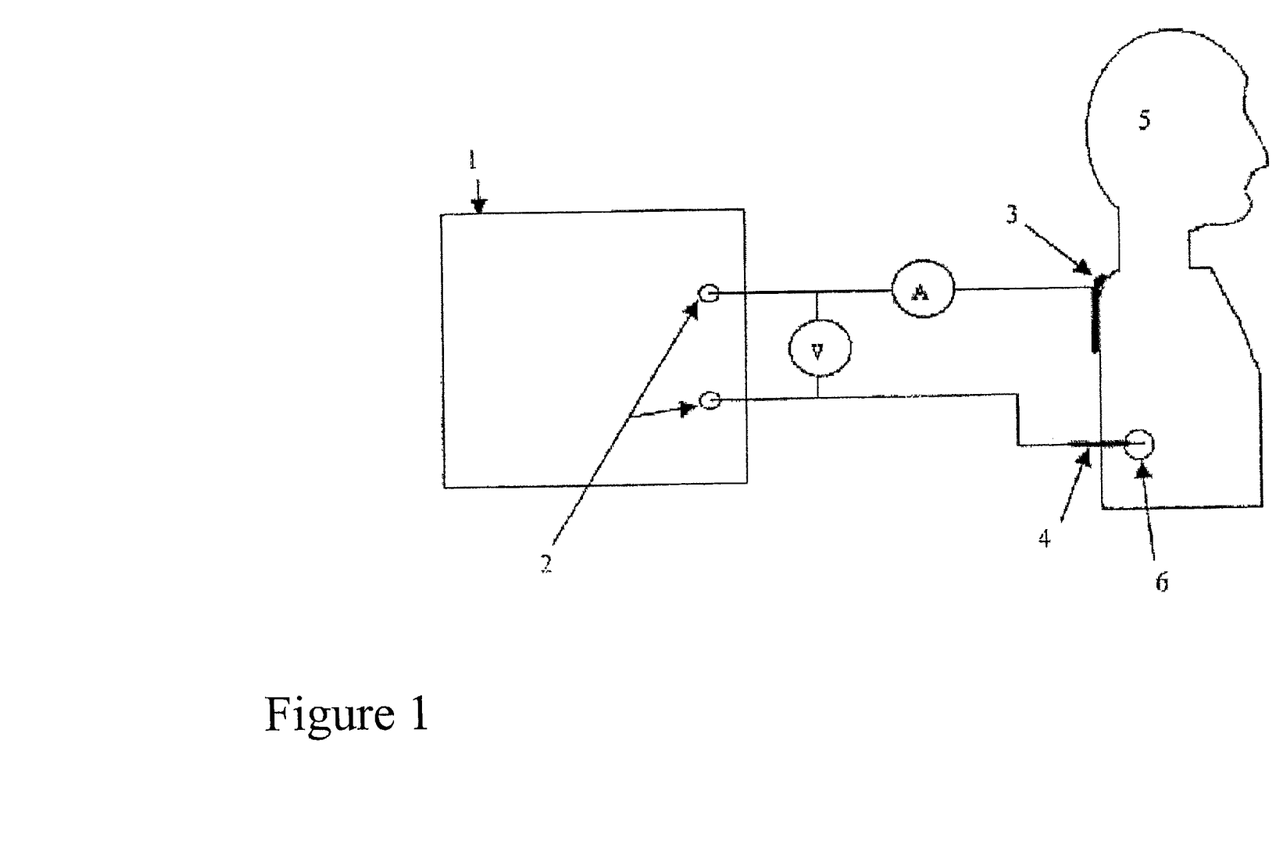
FIG. 1 is a schematic representation of a basic RF lesioning circuit

FIG. 1 illustrates a schematic of a basic RF lesioning circuit of common pain management signal generators. The basic components of the circuit include the electrical RF generator 1 which converts readily available electricity mains outlet to radiofrequency electricity and supplies the power to the output terminals 2 according to settings or a control algorithm; typically one output terminal is connected to a dispersive electrode 3 that is placed on the surface of patients body 5 and the other output terminal is connected to an active electrode 4 that is used to concentrate the current density in a target lesion location 6.

Figure 2:
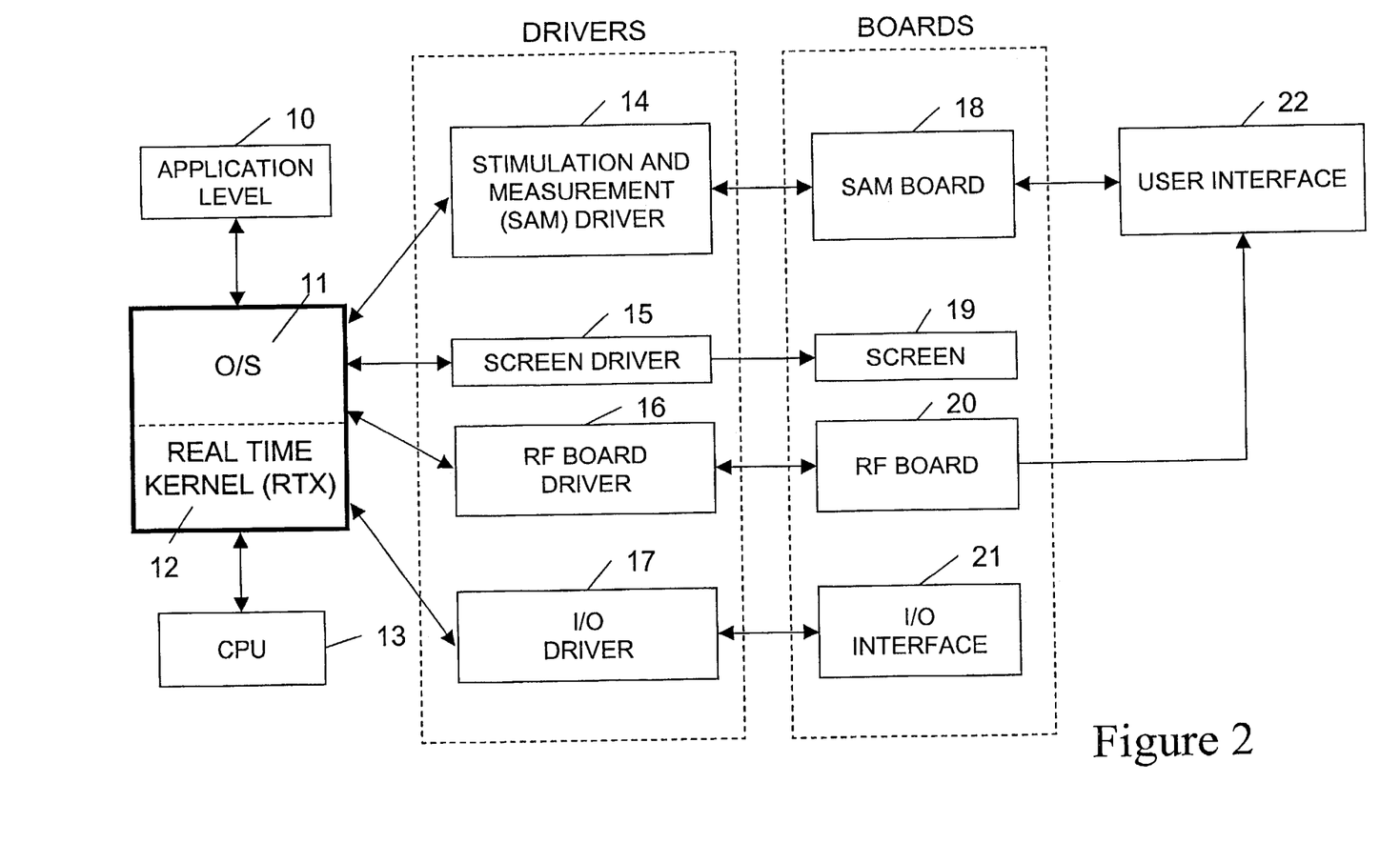
FIG. 2 is a block diagram of the architecture of an electrical signal generator.

FIG. 2 shows a schematic diagram of the interaction between the application, driver and board levels of one embodiment. The application level 10 contains all the software-coded modules that drive the functions of the generator. What follows are examples of functions that are performed and stored at the application level 10.

Temperature profile calculations are performed to convert the signal received from the temperature sensor in the RF probe into temperature values that can be used in the control algorithm. This is done through temperature lookup tables 36 that are preprogrammed into the application level. A signal transmitted from the temperature sensor is converted using temperature lookup tables 36 into a meaningful temperature value that can be displayed on the screen 34 to the user. This conversion is done at the application level 10 and the result is displayed on the screen 34 for the user to see.

Energy delivery to an application tool is governed by a classical control system (PID control) that is programmed at the application level 10. The inputs are temperature and power feedback loops that are connected to the temperature measuring probe 30. The output of the control system is the appropriate amount of voltage and current required to perform the programmed function.

The application level 10 is programmed to assign different functions to different user input controls such as switches and dials 37. This assignment of functions of the user input controls is done as soon as the application level 10 is turned on and is constantly modified depending on the current mode selected and the probe 30 that is attached to the generator. Algorithms are coded into the application level 10 to perform the selection of modes. These algorithms 33 take information from the Probe Type Detection function 32 of the generator to determine which probe 30 is attached and combine that information with user inputs introduced using user input controls 37 to determine the information to be displayed on the screen 34. When there is no user input as to the selection of the mode, the generator defaults to the most appropriate screen/mode for the probe 30 selected. The generator gets these screens from a graphical user interface library. This default to the appropriate mode and, thus, the display of the appropriate screen, makes the generator straight-forward to use. The modes are selected and the algorithm assigns the screens to be shown on the display 34.

Figure 4:
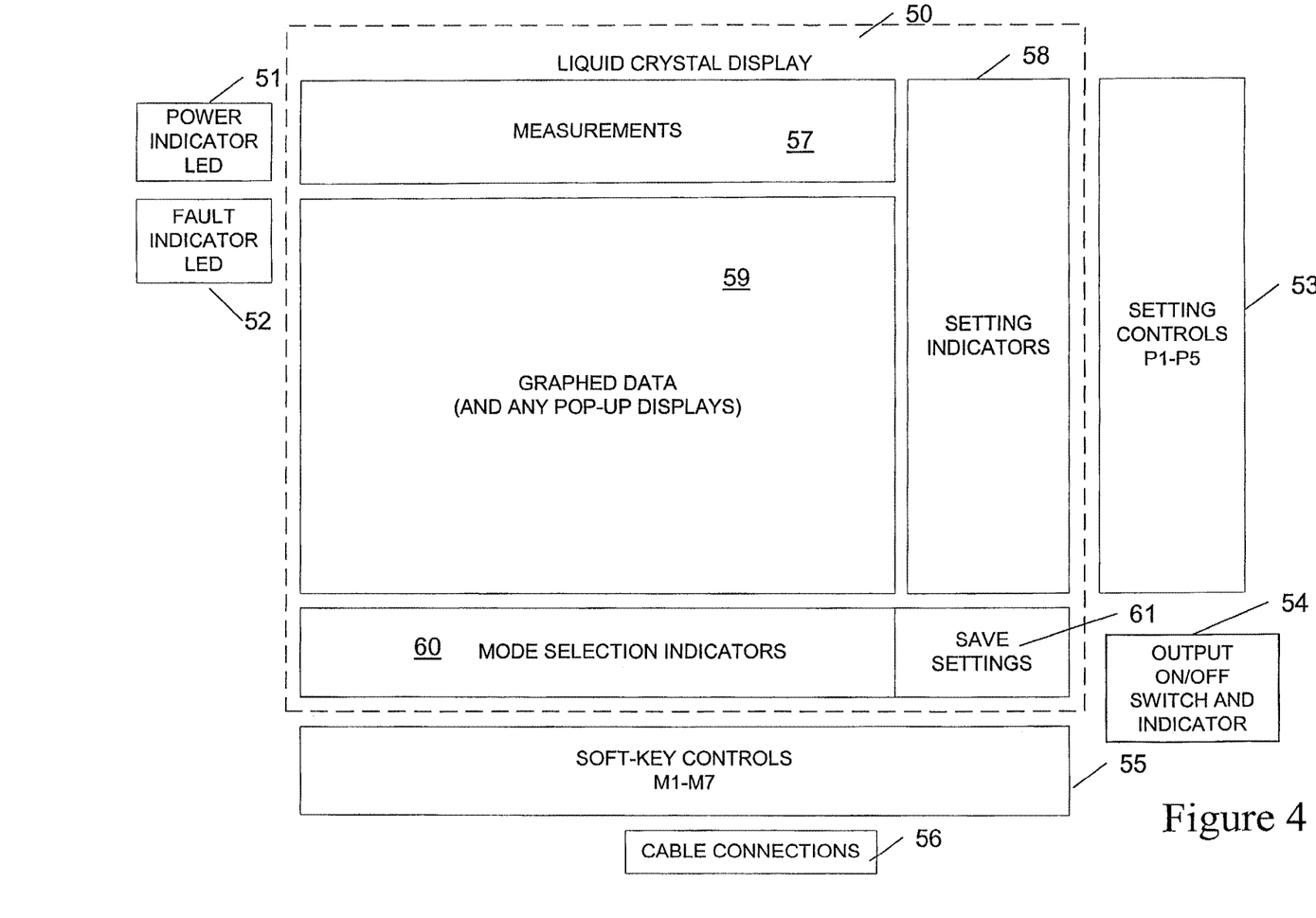
FIG. 4 is a schematic view of the components of a Front Panel User Interface for the signal generator.

With the display of the appropriate screen on the display 34 comes the assignment of the input settings 58 available to the user (see FIG. 4). These values are programmed into the application level 10 with the increments of settings that will be provided to the user through the display 34. These settings can be adjusted to meet the user requirements according to conditions predetermined by the algorithms in the application level 10. These predetermined conditions are based on safe and effective timings for the modification of the settings. When the user makes a change to the settings that are displayed by the settings indicators 58 he has the option of saving those settings as the default values. This save setting function is performed by the user's manipulation of an assigned switch 61 and the relay of that input to the software at the application level 10. The software (application level 10) stores the saved settings appropriately until the values are changed and saved.

Certain settings that are not used on a regular basis by the user are separated from the most commonly used settings and placed on a separate screen stored in the graphical user interface library in the application level 10. This simplifies the display and minimizes the settings that can be controlled on a more regular basis, thus increasing the ease of use. These less common settings can be changed within the limits of a predetermined range and can be saved by the press of an assigned switch. These less common settings are stored at the application level 10.

Messages displayed on the screen 34 are one of the ways that the generator interacts with the user in order to inform the user of the actions required or the status of the generator. These messages are called by a routine that is accessible by the application level 10 and they come in different categories including informational messages, error messages, and fault messages. This messaging system is preprogrammed at the application level 10 and the display of these messages is controlled by the constant monitoring of the status of the machine and the user inputs. This monitoring is synthesized by the application level 10 and information is taken from all input drivers 14, 15, 16, 17 and internal circuitry checks that are cycling at all times. When the application level 10 is notified of a user input command or a compromise in generator operation, the appropriate message is selected from the routine and displayed. These compromises in generator function can include exceeding software shut down limits that are defined in the application level 10, hardware problems such as faulty measuring systems, problems with the energy delivery system, conflicting settings by the user and any other internal problems that are contradictory to the application level 10 or any other level's operational requirements.

Parameters that are changing during energy delivery could also be stored at the application level 10. This way, a history of the lesion procedure could be extracted from the generator at a later date. This mechanism would involve transferring the variables that are being adjusted by the control loop into a storage device until it could be accessed and downloaded or transferred to an external device.

The application level 10 is directly linked to the operating system 11 (in some embodiments, a stRT Linux V1.00) and the Real Time Kernel (RTX) 12. Access to the central processing unit (CPU) 13 is provided through the operating system 11. No commands from the application level 10 can run without access to the CPU 13. The RTX 12 manages the access to the CPU 13 and controls the resources of the CPU 13.

Connected to the 0/S 11 is a system of drivers 14, 15, 16, 17 that are responsible for communication and direction of the four circuit boards 18, 19, 20, 21 of the generator. The four drivers are: the stimulation and measurement (SAM) driver 14, the screen driver 15, the RF board driver 16 and the I/O driver 17. The four boards of the generator are: the stimulation and measurement (SAM) board 18, the screen 19, the RF board 20, and the switches or I/O interface 21.

The SAM Board 18 is used for a variety of stimulation and measurement functions. The functions performed at the SAM Board 18 are stored in the driver and reported to the application level 10.

In one embodiment, the shape and the size of the stimulation pulses is determined by the application level 10 based on the settings of the generator and the energy delivery circuitry on the SAM board 18. This circuitry includes a switching mechanism that allows the pulses to be enabled or disabled based on commands from the application level 10. The presence of the stimulation output is detected at the circuitry and fed-back to the application level 10 for feedback to the user on the display 57. When a probe 30 is connected to the generator, the Probe Type Detector 32 function uses standard circuitry methods to assign the probe a DAC count that can be used to identify the probe to the application level 10.

As previously mentioned, the temperature lookup tables and conversions are done at the application level 10, but the analog circuitry that connects to the probe 30 is on the SAM board 18. This board sends information, through the driver 14, to the application level 10 on the voltages that are being read on the probe 30. That information is processed as previously discussed. It communicates with the operating system 11 through the SAM driver 14, shown in FIG. 2.

The screen 19 allows for display of real time measurements using a LCD display 34 and using graphics of measurements made by the SAM board 18 and RF Board 20. It displays, in real time, the measurements in digital and/or graphical form based on the information processed by the application level 10 and sent to the driver 15. The graphical user interface is accessed for the preprogrammed instructions on what to place on the screen in any particular situation dictated by the application level. It communicates with the operating system 11 through the screen driver 15.

The RF Board 20 generates the RF waveforms. It contains the power, transformers and electrical circuitry needed to supply electrical current at 460 kHz. The RF energy is applied to the probe 30 when the output is turned on 54. This RF board 20 is used to take voltage and current measurements and thus impedance and power indications are obtained from the registers on this board 20. It communicates with the operating system 11 through the RF board driver 16.

The switches or I/O interface board 21 is responsible for detecting short circuits for the settings user input controls 53, mode selection user input controls 55, output ON/OFF switch 54 and footswitch 40 for quick (20 ms) recognition of the user inputs. The user input controls 53, 54, 55 on the front panel (FIG. 4) are connected to the board 21 and the circuitry allows for the detection of a user input control press or hold. These user input controls 53, 54, 55 function through standard switching techniques, preferably soft touch switching techniques. The detection of user input at the board level is translated by the driver and provided to the application level 10 for processing and synthesis. It communicates with the operating system 11 through the I/O driver 17.

Figure 3:
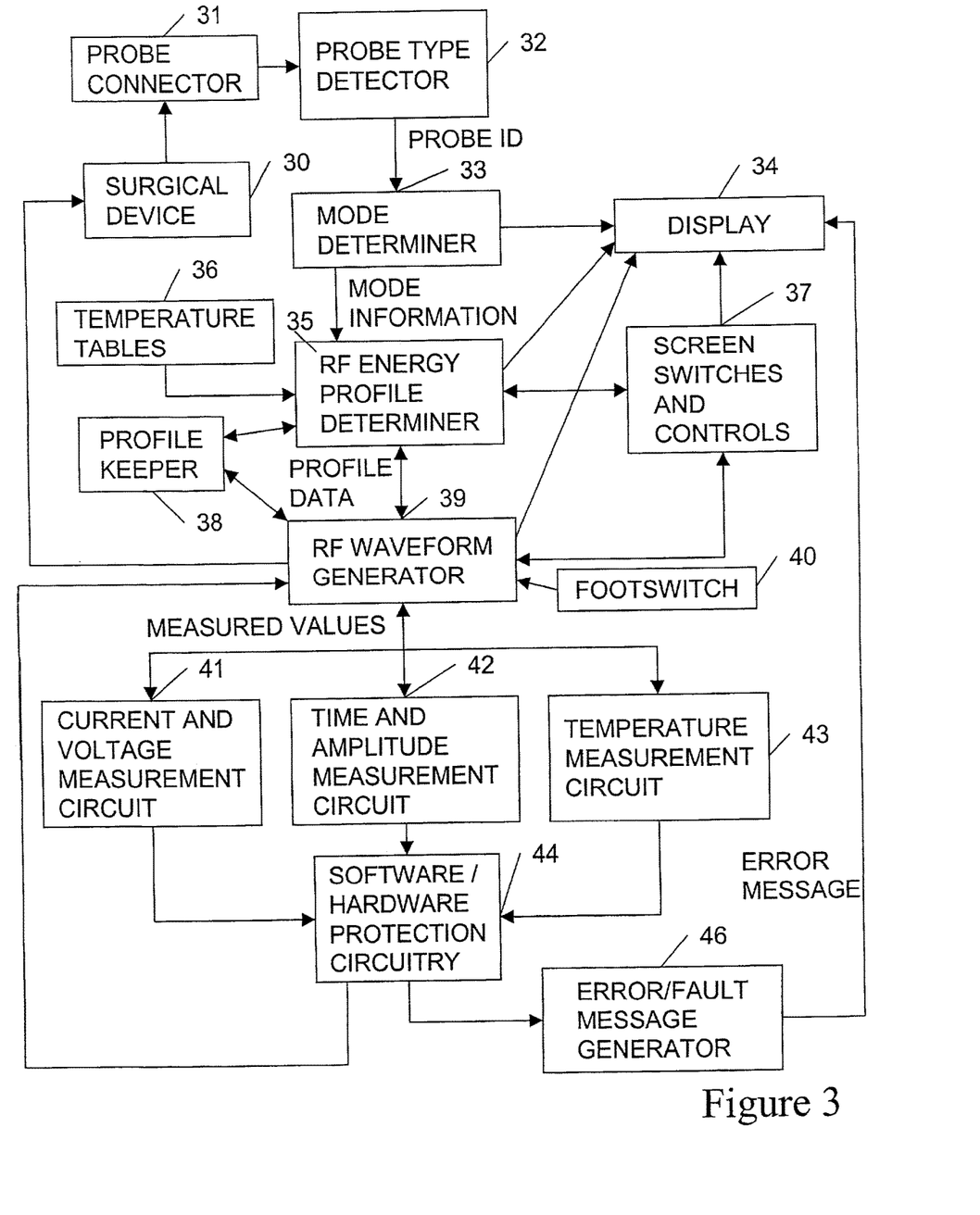
FIG. 3 is a block diagram of the main components of an electrical signal generator.

Referring to FIGS. 2 and 3, the screen 19 and user input controls 37 are the input and output devices that communicate with the user. The probe 30 and connector cable 31 are switched between the RF board 20 and the SAM board 18 depending on the desired function of the probe 30. The physician will be using the probe 30, the connector cable 31, the display 34 and the user input controls 37 to interact with the RF generator.

This system is very flexible in the division of labor between the application level 10, the driver level 14, 15, 16, 17 and the board level 18, 19, 20, 21. Although it has been found to be most efficient to apply most controls at the application level 10, it is possible to put any or all of the functions at different levels. Any combination of task division including these three levels would be an improvement in flexibility and functionality on the prior art technology. For example, the Pain Management generators on the market today tend to have the control of the temperature profile at either the board level or the driver level. These would be considered low level controls and would make it difficult to incorporate changes to the device without changing a lot of the hardware in the generator.

Preferred Radiofrequency Waveform Specifications

A continuous radiofrequency waveform can have a set frequency (for example, 460 kHz) and shape (for example, quasi-sinusoidal). The amplitude of this waveform can be modified through user inputs using the user input controls 37, in combination with or independently of the PID control of the output, upon energy delivery, depending on the mode selected. In the preferred embodiment, an Automatic Temperature mode performs PID control on the temperature inputs/monitoring and power outputs/monitoring. In the case of Manual Power mode, the generator allows the user to control the power based on the temperature measurements. During standard RF procedures, the RF wave is continuous. In pulsed procedures, the switch settings and the application level 10 determine the delivery profile.

The RF waveform is generated on the RF board 20, interfaced to the 0/S 11 by the RF driver 16, and controlled by the application level 10 in the form of PID control systems and sampling of switch values. The RF waveform is delivered to the probe after the application level 10 dictates a series of relays that must take place to switch the probe 30 to the patient.

FIG. 3 is a block diagram of the preferred main functional components of the generator. Functional components may be implemented at any level (application 10, driver or board levels) of the generator architecture and they can be divided between levels of the architecture. It will be understood that some of these components are optional to the operation of the generator and are simply shown since they form part of the preferred embodiment.

A medical device 30 is connected to a connector cable 31, which is in turn connected to the generator cable connections 56 which has a functional component that acts as a Probe Type detector 32. The Probe Type detector 32 detects which probe 30, of a host of compatible devices, has been connected to the generator and sends a probe identification to a mode determiner 33. The mode determiner 33 uses the probe identification to determine in which mode the generator is to operate. The mode information is sent to the display 34 for display of the main mode interface. The mode information is also sent to the RF energy profile determiner 35 which uses temperature look up tables 36 to update the display 34 and the screen user input controls 37 labels and values. In turn, the screen user input controls 37 can also update the display 34 of the labels and values for the user input controls 53, 55 on the screen 19. When the values of the user input controls 53, 55 (displayed on the graphical user interface 58, 60) are changed by the user, the updated values are sent by the screen switches and controls 37 to the RF energy profile determiner 35 for the adjustment of the profile. The profile can also be stored using a profile keeper 38 which stores the profile parameters transmitted by the RF energy profile determiner 35.

The RF energy profile determiner 35 then sends the RF energy parameters to the RF waveform generator 39 which makes the appropriate calculations and generates the RF waveform with the proper amplitude, frequency and time. The footswitch 40 is used to turn on or off the RF generation. The RF waveform generator 39 can send data to the display 34 to display a graphical representation of the RF waveform to be generated. The profile keeper 38 can also keep in memory the RF waveform parameters. The RF waveform generator can also update the screen switches and controls 37.

As the RF energy is being delivered, the current and voltage applied at the medical device 30 is measured by a current and voltage measurement circuit 41 or using the current and voltage that is being delivered. The current and voltage measurement receives the RF waveform parameters from the RF waveform generator 39 and compares the measured current and voltage to the required current and voltage as determined by the control algorithm. The difference between the measured and expected values is sent to the software/hardware protection circuitry 44 which compares the differences received with cut off values and triggers an error generation if necessary. Similarly, the time and amplitude is measured by a time and amplitude measurement circuit 42 and the temperature is measured by a temperature measurement circuit 43. All measurement circuits 41, 42 and 43 can feedback their readings to the RF waveform generator 39 for adjustment of the zero values and correction of the parameters.

The software/hardware protection circuitry 44 receives all differences between the expected and measured values and is responsible for triggering an error generation, if necessary. If an error generation is necessary, the software/hardware protection circuitry 44 sends a trigger message error/fault message generator 46 and shuts down the generation of RF energy. The error/fault message generator 46 then sends an error message to the display 34 for display to the user. The software/hardware protection circuitry determines whether the hardware components should be protected against potentially harmful conditions. If so, it also triggers the error/fault message generator 46 to send an error message to the display 34 and manages the protection of the hardware components.

In some embodiments, the system provides for the management of the values specified by the user for the treatment profiles. See FIG. 4 for a schematic look at the front panel user interface for the generator.

The input/output interface board 21 is given information on the allocation of variables to user input controls based on the screen 19 that is selected. The application level 10 determines the range of the variables and the increments by which they can be changed by the user. The switch board 21 and driver 17 monitor the values that the user sets by detecting short circuits at the soft touch key interface 53, 55. The information on the variable values is processed and the application level 10 instructs the CPU 13 to perform mathematical calculations for the treatment profile. These treatment profiles are based on the physicians requirement that a lesion of a particular temperature (SET TEMP) is maintained for a given time (TIME). Additional specifications can include pulse duration, pulse rate, power limit on the procedures or a special ramp rate for attaining the wanted temperature. Constant monitoring of the switch board 21 and switch driver 17, as directed by the real time kernel 12, allows for real time changes of the system variables.

In order to maintain the user specified treatment profile, the application level 10 uses system feedback information from the SAM Board 18 temperature measurement for control of RF output. The PID control algorithm in the application level 10 indicates, for example, a 20 ms temperature measurement frequency. The operating system 11 communicates with the SAM driver 14 to obtain the ADC count from the SAM Board 18 circuitry resulting from the analog voltage supplied by the probe 30 at the treatment site. This value is sent to the application level 10 where the probe identification and ADC count for temperature are combined together to get a temperature value in degrees from the temperature lookup table 36 for the appropriate probe 30. This temperature can be displayed on the screen 57 through the screen Driver 15 and/or can be sent to the PID controllers to adjust the power application for RF delivery.

The maintenance of the desired temperature at the treatment site is performed using PID control techniques. The desired temperature of the system is compared to the actual temperature and the changes in current or voltage are determined and applied to the system.

For example, in automatic temperature mode, the generator does automatic temperature control using a PID control system combined with a power control system to ensure that an appropriate amount of power is supplied and to ensure that the user specified treatment profile is delivered.

The front panel user interface (FIG. 4) of the preferred embodiment can be described as follows. A power indicator LED 51 indicates if the power if is turned on. A fault indicator LED 52 indicates if a fault has been detected. The liquid crystal display 50 comprises five general areas. The measurement area 57 is where values measured are displayed. A graphed data and pop up display area 59, a setting indicators area 58, a mode selection indicators area 60 and a save settings area 61 are provided. Hardware setting controls P1 to P5 53 are provided. An output on/off indicator 54, a series of soft key controls M1 to M7 55 and cable connection outlets 56 are also provided on the front panel user interface. The setting controls P1 to P5 53 are inputs to the setting indicators 58. The soft key controls M1 M7 55 are inputs to the Mode Selection Indicators 60.

Error/Fault Detection (Cut Off Mechanism)

Figure 6:
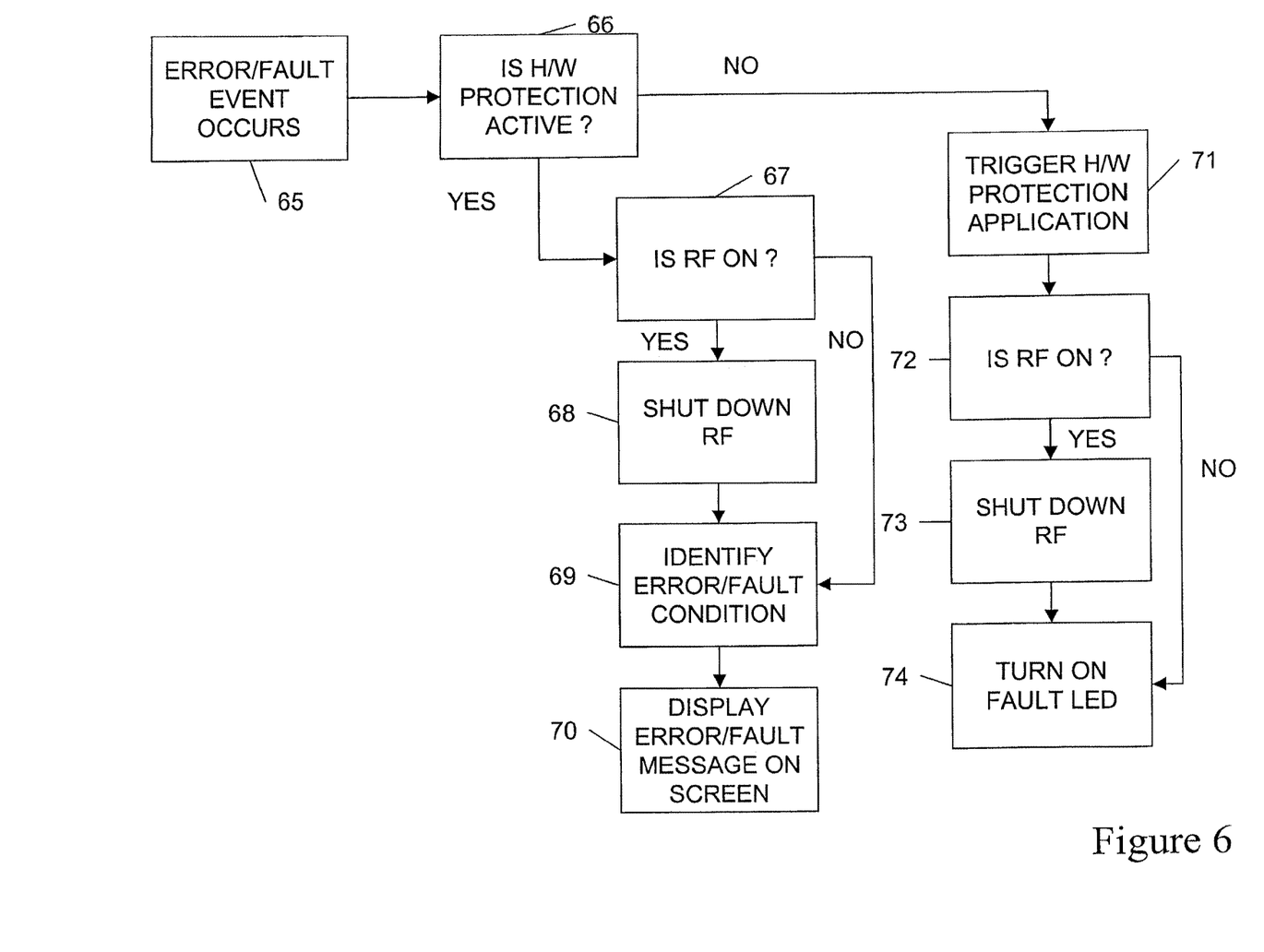
FIG. 6 is a flow chart of the error/fault detection and control process.

FIG. 6 is a flow chart of the steps of the error/fault detection mechanisms. Software shutdown limits are designed to detect any problems before they affect the components at the hardware level. The application level 10 gets information of the Error/Fault event 65 and determines what error/fault code will be displayed to the user. This information is passed from the application level 10, to the screen driver 15 and is then displayed on the screen 59. The error events are all preemptive events in the RTX 12 and will take highest priority at the processing level if they occur.

If the software fails at any time, the machine is designed to shut down RF energy immediately. This mechanism is commonly referred to as a watchdog hardware protection application 66 and it detects software shutdown. If the watchdog hardware is not toggled by the software every 20 ms then the watchdog application is triggered and has no choice but to shut the down the RF Output 71, 72 and 73 right at the level of the RF board through a circuit cut-off. A fault led is lit 74. In addition, an informational message is retrieved from the application level and displayed on the screen 59 to notify the user of the problem and the potential solution. In cases where software shutdowns are implemented it is the intention that extra information for the user would allow for them to troubleshoot the event and determine how to proceed.

The driver status is verified every 20 ms by a CHECKSUM that is performed on the data sent by the driver. If there is an inconsistency in the checksum, the application level 10 triggers an error. The RF generation is shut down 68. The error/fault condition is identified 69 and the error/fault message is displayed 70 on the screen.

It is also possible to deal with error/faults at any level throughout the system. For example, certain errors could be generated from the RF board 20 while others could be generated at the SAM board driver. The division of labor has infinite combinations and is best based on the functionality and efficiency proposed by the system. No matter where the error is generated, the system has the intelligence to relay that information to the application level and access the informational message that will allow the user to troubleshoot.

Examples of software shutdown limits are as follows:

measured impedance smaller than 25 or greater than 1000 Ohms, measured temperature greater than the set temperature by 5° C. for 5 seconds or by 10° C. for 1 second, measured RF power greater than the set RF power multiplied by 1.5 plus 5 W for 100 ms, measured RF power greater than the set RF power multiplied by 1.5 plus 5 W for 1 s, or measured RF voltage greater than 170 Vrms and a measured RF current greater than 0.9 Arms.

Examples of hardware shutdown limits are as follows:

measured RF Power greater than 60 W±5%, measured RF voltage greater than 200 Vrms±5%, measured RF current greater than 1 Arms±5%, stimulation current greater than 40 to 44 mA, and stimulation voltage greater than 11 V.

Probe Identification

A probe 30 is preferably attached to the generator via a connector cable 31. The connector cable 31 is used in order to extend the distance that the physician can work away from the generator, and to provide flexibility in which probes 30 can be connected. For example, different probes 30 may have different connectors 31, but any probe 30 can be attached to the generator using the properly designed connector cable 31. The connector cable 31 comprises a cable attached to two electrical connectors. These connectors are designed to match the appropriate probe plug-in at one end and the appropriate generator plug-in at the other. Connector cables create flexibility in probe compatibility and create a workable extension of the probe for physicians' use.

In the preferred embodiment, the port 56 on the generator where the connector cable 31 is attached is a standard medical connector. It is possible to make connector cables 31 with the matching medical connector for any probe 30 that could be attached to the generator. Because this interchangeability is desirable, a Probe Type Detector system is incorporated. The Probe Type Detector 32 allows a variety of different probes 30 to be connected to the generator, initializing appropriate programmed functions relevant to the probe detected. For example, relevant treatment modes are provided to the user when a particular probe 30 is connected.

The connector cable 31 contains the technology that allows the Probe Type Detector 32 to identify the probe. Specifically, on the end of each connector cable that connects to cable connection 56, there is a medical 14 pin connector. In all compatible cables, pins 1, 2, 3 of the 14 pin connector are the identity pins. These identity pins can be shorted together or have a resistance attached across them in order to allow the generator to identify what probe is going to be attached.

The Probe Type Detector 32 circuitry consists of resistors connected in series. This connection creates a voltage divider that is modified by reading the voltage coming from the three identification pins. This voltage is changed by creating electrical shorts between pins or by connecting resistors across them. The resulting voltage is converted to an ADC count through an analog to digital converter and each probe type is assigned its own ADC count.

In the preferred embodiment, the ADC count that corresponds to the cable 31 attached is written to the Stimulation and Measurement Board 18 ADC register. This register value is sent through the driver level to the application level 10 and to the operating system 11. It is maintained by the application level 10 in order to detect cable connection and disconnection and to use the information for temperature look up tables.

Figure 5:
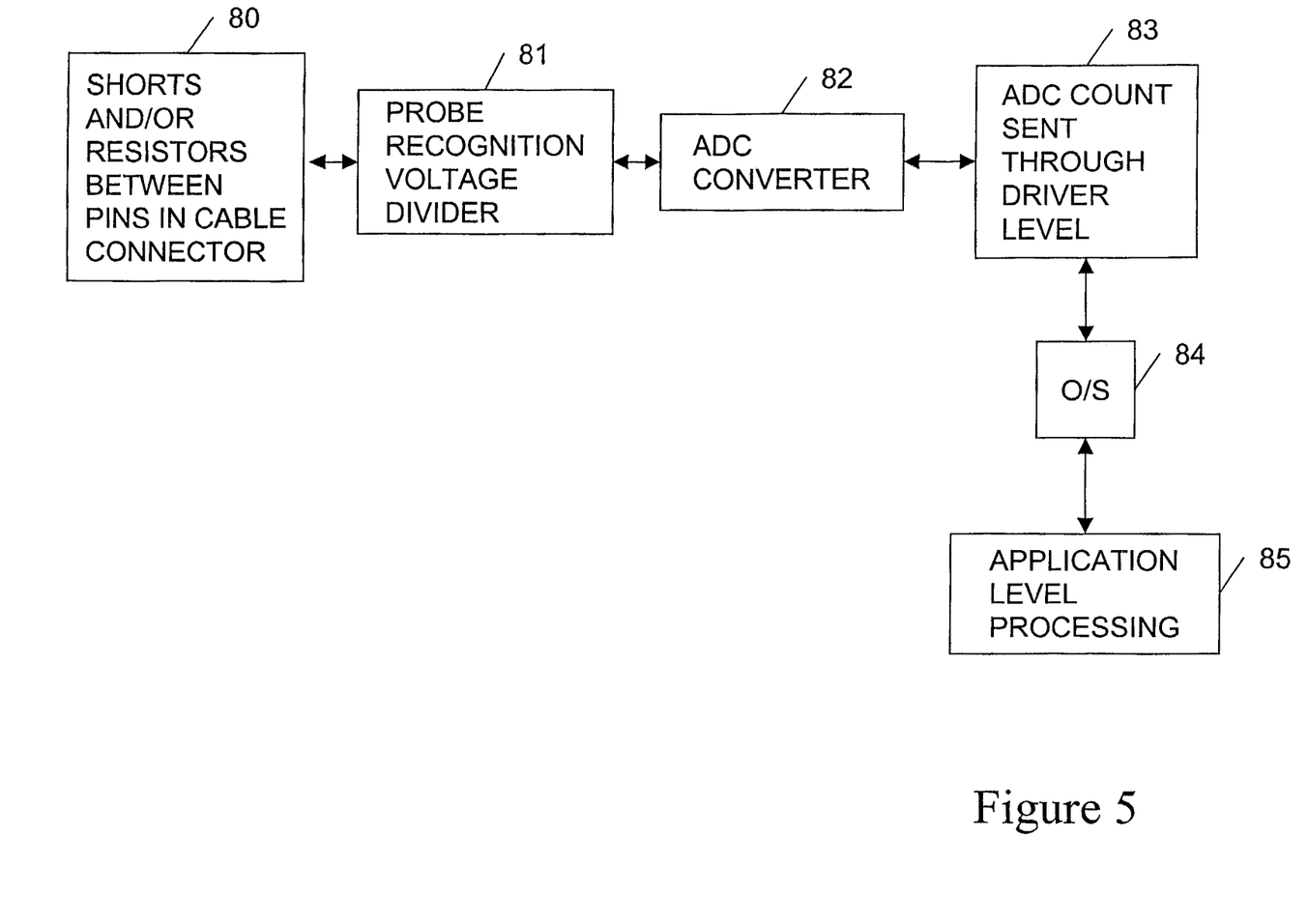
FIG. 5 is a flow chart of the probe recognition process.

FIG. 5 is a flow chart of the steps carried out to identify probes. Shorts and/or resistors are used between pins of the cable connector to create a unique identification corresponding to a type of surgical device 80. The probe recognition voltage divider circuitry 81 calculates the voltage across the pins. The ADC converter converts this data 82 to an ADC count. The ADC count is sent through the driver level 83 to the operating system 84 which then sends the appropriate data to the application level processing 85 which can map the appropriate profile and/or mode to the probe 30 that is connected.

Figure 7:
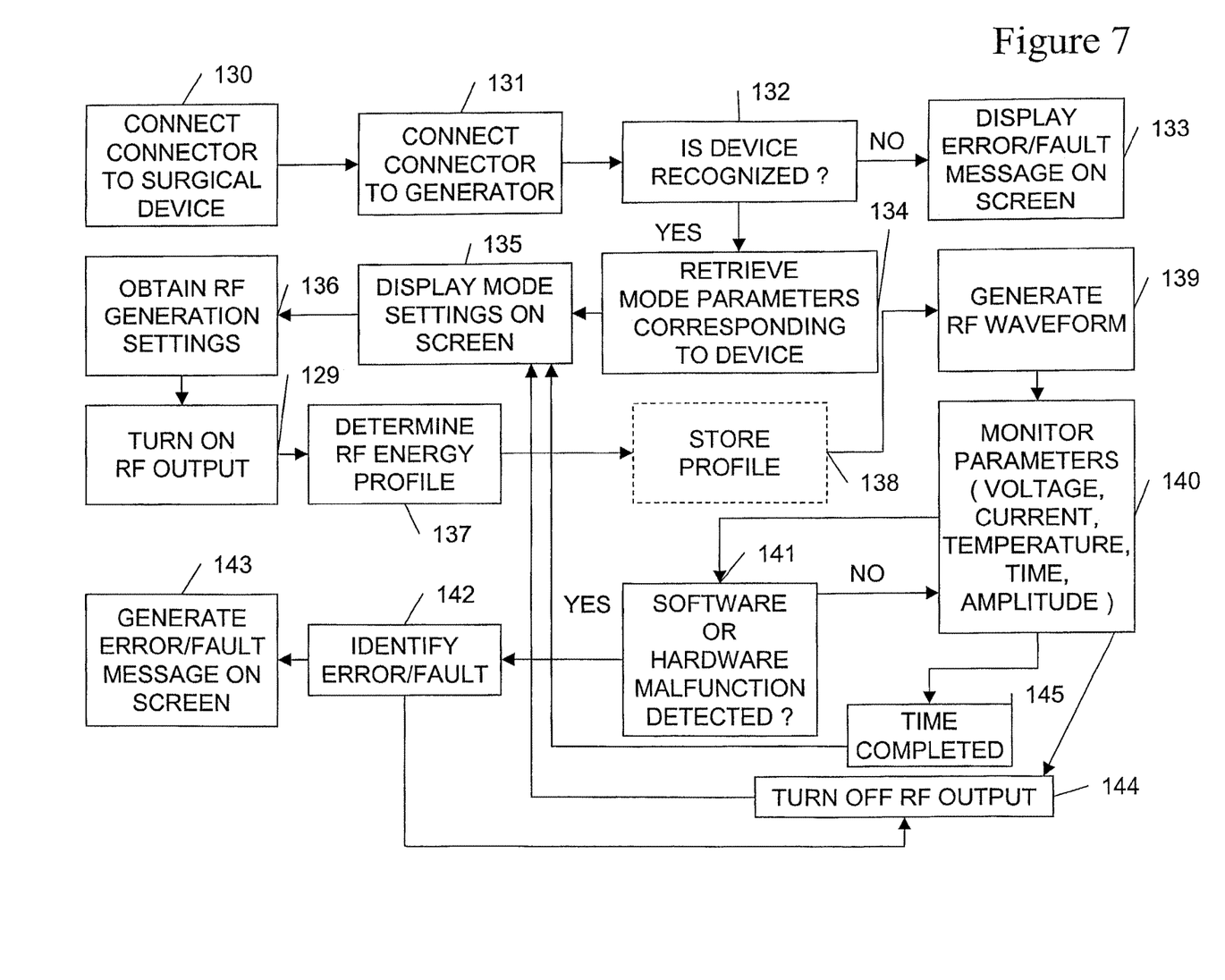
FIG. 7 is a flow chart of the main steps carried out while using a medical probe signal generator.

FIG. 7 shows a flow chart of the main steps carried out when using the generator of the preferred embodiment. A compatible probe is connected to an appropriate connector cable 130. The connector cable is connected to the generator 131. Then, the Probe Type Detector determines if the probe is recognized 132. If the probe is not recognized, an error/fault message is displayed on the screen 133. If the probe is recognized, the treatment mode parameters corresponding to the probe are retrieved 134. The mode settings are displayed on the screen 135. The RF generation settings are then obtained from the user inputs 136. The user accepts the settings and proceeds by turning on the Output 129. When this is done the RF energy profile is determined 137 and can be stored 138. The RF waveform is generated 139 and the parameters (such as voltage, current, temperature, time and amplitude) are monitored 140. If a software or hardware malfunction is detected 141, the error/fault is identified 142 and an error/fault message is generated on the screen 143. If there is no malfunction, then the monitoring of the parameters continues 140. Furthermore, the RF output can be manually turned off 144 anytime during RF output. RF output terminates automatically when the predetermined parameter, time, is complete 145. When RF output is stopped, either manually or automatically, the display on the screen returns to show the mode settings 135 after a brief pause.

Treatment Profile Implementation and Control Mechanism

The treatment profile, or the manipulation of temperature according to treatment time, is commonly specified by the user in terms of SET TEMP (temperature reached by the tissue) and TIME (duration of power application). With the software control of the generator screen 19, only the treatment variables required for a specific mode of treatment are presented on the screen 19 and the values are easily adjustable before a procedure. The application level 10 selects an appropriate treatment mode relevant to the connected probe and user input control allocation allowing settings to remain adjustable throughout the procedures or to be made non-communicating to eliminate the possibility of changes.

The application level 10 has the capability to manage data for the user. For example, the modes and settings used can be saved. The user can input and save comments about the procedure and the patient's response to stimulation. The user can input and save treatment data such as time, temperature, impedance, power, voltage, current, set temperature, and set power. User information such as names and preferred settings can also be stored. Patient information can be saved including: name, patient identification number, address, phone number, fax number, regular physician, diagnosis, medical history. The data saved could be organized by the application level 10. The storage of these parameters is done using a hard drive or flash disk in the generator or real-time transfer of parameters through a data transfer port. Those skilled in the art will realize that there are a variety of computer tools available to perform this data transfer, but the ability to store the information that will be pertinent for a pain physician in order to facilitate ease of documentation, due to the flexibility in the software architecture of the system is unique to this system. All data entry would be done using a standard computer or a combination of keys on the generator.

Preferred System Configuration Specifications

Preferably, the product software is to run on a 486 66 PC/104 by Advantek with 16 MB of RAM and its ROM is to be 32 MB of Flash EPROM. The display is a 640×480 flat panel LCD in VGA mode.

The operating system should be a stRTLinux V1.00 and the compiler should be a gcc version egcs 2.90.29-GNU project C compiler.

Details of the Components of the Generator and Its Tools

The mode is basically a function that the operator (i.e. physician) wants to perform on the patient. The following is a list of examples of interventional pain management modes that can be made available in the generator.

Voltage stimulation of nervous tissue: Voltage stimulation is the most common way to stimulate nervous tissue. Stimulation is used to check the placement of the electrode by trying to elicit specific responses from the nerves/patient. This is accomplished by sending a signal that is similar to the electrical signal used by either a sensory nerve or motor nerve. If the electrode is close to a nerve, a noticeable response is elicited. Sensory stimulation is done at low frequency, typically 50 Hz, in order to reproduce the pain that the patient feels. Motor stimulation is done at a low frequency, typically 2 Hz, to ensure the absence of a motor response (a motor response would indicate that you are too close to a motor nerve, which is the incorrect position). Therefore, by reproducing pain using sensory stimulation and applying motor stimulation without eliciting a motor response the physician can determine that the electrode is close to the pain transmitting nerve and not near a motor nerve. And thus, when the intervention is preformed the correct nerve will be affected. The frequency range used for both sensory and motor stimulation is within the range of frequency used by the nervous system and is often termed physiological frequency range. In this mode the physician can increase the voltage to stimulate the patient.

Current stimulation of nervous tissue: This mode has the same function as Voltage stimulation but allows the physician to use current manipulation. This will be most applicable to research settings.

Automatic Temperature RF lesioning: This is a lesioning mode, which means that RF is applied to create a zone of heating. The temperature in this heated zone is set by the user and controlled by the generator. This is a neuro-destructive technique, designed to ablate the nerve so as to intervene with the transmission of a pain signal. This mode uses a Power PID control system to maintain a temperature profile set by the physician prior or during the application of RF energy. This mode applies a continuous waveform of radiofrequency energy over the entire treatment time.

Manual RF lesioning: This mode has the same function as the Automatic Temperature Lesioning mode, ablation of nervous tissue at neuro-destructive temperatures set by the physician. It can be used for research and development of new lesioning parameters or instead of the automatic mode. It involves the manual increase of the Power in order to obtain and maintain the desired temperature for lesioning. This mode applies a continuous waveform of radiofrequency energy over the entire treatment time.

Pulsed RF lesioning: In this mode, there is a non-continuous application of energy (pulsed waveform) that is intended to allow the tissue to maintain a lower temperature (non neuro-destructive) while still allowing for application of voltages and current over the treatment time. The goal is to manipulate an electrical field surrounding the nerve and create some beneficial effect on the painful nerve without destroying it with heat.

Intradiscal lesioning: This mode has a different intended use. This mode is used for therapy involving intervertebral discs. There are a variety of different mechanisms of therapy that make this technique effective but they are restricted to accessing the intravertebral disc with the correct probe and applying RF to a resistive element which then radiates heat to the surrounding tissue or through direct application of RF energy to create heating of the tissue.

The most common modes that are currently used for treatment in the field of Interventional Pain Management are: Voltage Stimulation followed by Temperature Lesioning for nervous tissue and Intradiscal lesioning for Intravertebral discs.

Treatment methods in pain management are usually procedures that are relatively repeatable by the physician. Certain variables will change in the hands of different physicians and with the treatment of different patients, but there are standard operations that the equipment used for the treatments must allow. For example in facet joint denervation, the physician must have access to equipment that has stimulation and lesion capabilities. These capabilities are considered treatment methods. The treatment methods that are available in the preferred embodiment are grouped by function so that the user can easily move between the appropriate treatment methods while avoiding the information for the treatment methods that they do not intend to use at that point. As previously mentioned, the physician selects their treatment mode either by plugging in the appropriate probe (allowing the Probe Type Determiner to select the treatment mode) or by manually selecting the mode based on the available selections.

Flexibility and Adaptability of the System and the User Interface

The other modes present in this generator are gaining acceptance and use in Pain Management. Some of these modes are not well established but are used for research or for teaching purposes. The benefit of this system is that these treatment modes can be incorporated in this generator without adding more user interface controls because of the CPU control algorithms and software input control systems. There are many treatment modes currently being developed that would also be easily incorporated into the existing generator due to the fact that the architecture is software driven and flexible. The output on a Flat Screen display and the graphical user interface can be easily modified when these treatments are added to the system without compromising the ease of use. In addition, the informational messages can be maintained for the user and can be easily changed to include information appropriate for future treatments.

The table below shows examples of compatible probes, the modes they elicit and the adjustable settings for the modes. In the Adjustable settings column, a star "*" before a setting represents a setting that is adjusted in the advanced settings because it is seldom adjusted.

TABLE 1

Compatible probes, modes they elicit and adjustable settings for the modes

| PROBES | MODES | ADJUSTABLE SETTINGS |
|---|---|---|
| Thermocouple monopolar RF probe | Voltage stimulation mode | Stimulation rate Pulse duration Voltage |
| | Current stimulation mode | Stimulation rate Pulse duration Current |
| | standard RF, Automatic Temperature mode | Set temperature Time Ramp time Power limit |
| | standard RF, Manual Power mode | Temperature limit Time |
| | pulsed RF mode | Set temperature Time Pulse duration Pulse rate Ramp time Power limit |
| Thermistor monopolar RF probe | Voltage stimulation mode | Stimulation rate Pulse duration Voltage |
| | Current stimulation mode | Stimulation rate Pulse duration Current |
| | standard RF, Automatic Temperature mode | Set temperature Time Ramp time Power limit |
| | standard RF, Manual Power mode | Temperature limit Time |
| | pulsed RF mode | Set temperature Time Pulse duration Pulse rate Ramp time Power limit |
| Intradiscal thermal probe | intradiscal lesioning mode | Peak temperature Time Initial temperature Initial time Ramp rate Power limit |

For example, referring to Table 1, if a Thermocouple monopolar RF probe is connected, the generator will allocate a button for selection of each of the 5 available modes that are applicable to the probe. In this case the available modes are Voltage stimulation mode, Current stimulation mode, standard RF, Automatic Temperature mode, standard RF, Manual Power mode, and pulsed RF mode. The available modes and allocation of buttons is indicated by the screen. When a mode is selected, for example Automatic Temperature mode, the generator will allocate a button for adjustment of each of the adjustable settings. In this case the adjustable settings are: Set temperature and time. Typical values are 80° C. and 90 seconds. The adjustable settings, values and allocation of buttons are indicated by the screen. Additionally, the screen can show graphical information of certain aspects of the power delivery in real time and instantaneous values. For example, as power is being delivered the temperature, power and impedance are graphed with time and the instantaneous values are also displayed.

Preferred Method of Operating the Electrical Signal Generator

User Interface According to Probe Recognition

The electrical signal generator is powered on and if nothing is connected to the cable connections 56 a message is displayed that prompts the user to connect a medical instrument to its cable and connect the cable to the electrical signal generator. The electrical signal generator is in a state called Standby State. In this state, the Advanced Settings screen can be accessed by pressing a button.

Up until the power output is activated, the physician can place the medical instrument in the patient using methods known to those skilled in the art.

A compatible medical instrument (i.e. probe) is connected to the cable connections 56 of the electrical signal generator. Automatically, the electrical signal generator enters a default mode, which is most commonly used first with the connected medical instrument. For example, when a thermocouple monopolar RF probe is connected, the electrical signal generator automatically enters voltage stimulation mode. When the electrical signal generator has entered a mode and power output has not been initiated it is in Ready State.

The user input controls (buttons and dials) are multifunctional and the functions depend on the probe connected. A screen is displayed that indicates which mode is selected, which modes are available for the connected medical instrument, and which buttons are used to select the modes. This information is indicated by displaying all available mode titles in boxes next to the allocated buttons and highlighting the mode selected. Adjustable settings applicable to the connected medical instrument and selected mode are also displayed. The user has the option to go to any of the modes applicable to the medical instrument connected.

User Interface According to Mode Selection

When a compatible probe is connected to the electrical signal generator the user has the option to access any of the applicable modes by pressing buttons. In each mode, the user can adjust settings applicable to that mode. The functions of the user input controls depend, also, on the mode selected. A screen is displayed that indicates which settings can be adjusted for the selected mode, which buttons are used to select the modes and the values of the adjustable settings. This information is indicated by displaying all of the adjustable setting titles and their values in boxes next to the allocated buttons. In certain modes the adjustable settings are only active in a certain state (i.e. adjustable in "ready" state and not adjustable in "on" state or vice versa). This is indicated by highlighting the active setting boxes. When the user is in the desired mode, the relevant adjustable settings can be altered. Then the power output is activated by pressing the Output On/Off Switch and Indicator 54. The electrical signal is delivered to the medical instrument based on the mode and adjustable settings. Some settings may be adjusted while the power output is activated. The screen will also display a graphical representation of various aspects of the delivered electrical signal in real time and instantaneous values. The graphical representation is also dependent on the mode selected.

When in voltage stimulation mode the adjustable settings are stimulation rate, pulse duration and voltage. The settings indicators 58 also display the values of the adjustable settings. In every mode the screen also identifies which user input controls 55 are allocated for switching to other modes that are applicable to the connected probe. For example, when a thermocouple monopolar RF probe is connected, voltage stimulation mode, current stimulation mode, automatic temperature lesioning mode, manual power lesioning mode and pulsed lesioning mode are identified in the mode selection indicators 60 and can be accessed by pressing the user input controls 55. Other modes can be accessed by pressing the appropriate user input controls 55 when in Ready State. When the mode is changed the screen changes to display the appropriate settings indicators 58 and other displays such as graphs 59 and measurements 57.

Therefore, from Ready State of the default mode the user has the option to enter a different mode, alter the settings in the present mode or, if satisfied with the settings, activate the power output. Typically, if a thermocouple monopolar RF probe is connected the electrical signal generator would automatically enter Ready State of the Voltage Stimulation Mode and a physician would stay in this mode and use the settings that are already set and activate the power output. When the power output is activated, by pressing the Output On/Off switch and indicator 54, the electrical signal generator is in the On State. In the On State, the electrical signal is delivered to the connected medical instrument according to the mode and settings. Certain settings are adjustable during the On State. Typically, a physician would use Voltage Stimulation Mode to apply a signal that would stimulate a sensory nerve (50 Hz, 1 volt). If the symptomatic pain is reproduced by applying this signal, then the medical instrument is close to the target nerve. The Voltage Stimulation Mode is also used to apply a signal that would stimulate motor nerves (2 Hz, 2-3 volts). If a motor nerve is stimulated, the medical instrument is too close to a motor nerve and must be repositioned.

Saving User Profiles

For each compatible medical instrument, there are available modes. For each medical instrument and mode, there are adjustable settings. To save time, all of the adjustable settings can be set to preferred values and saved so the next time the same type of medical instrument and mode is used, the preferred values are automatically recalled. This can be done for each medical instrument type and mode that the user accesses, thereby creating a user profile. Furthermore, several user profiles can be saved for different situations or multiple users.

When the electrical signal generator is in Standby State the user can choose a user profile by pressing a button whose function is indicated on the screen. Alternatively, a medical instrument can be connected without choosing a user profile and the last user profile that was in operation is recalled. The first time a user accesses a mode, the adjustable settings are set to desired values and saved to the user profile by pressing a button indicated by the screen. The next time the user accesses that mode the saved settings are recalled and displayed. The user has the option of changing the adjustable settings again if desired. But, since the user profile is recalled, the user is likely satisfied with the settings and can simply activate the power output.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An energy delivery system, comprising:
a connector cable configured to releasably couple an energy generator with a plurality of medical treatment devices, the connector cable comprising an identifier;
the energy generator, comprising a processor, memory and a display screen, configured to:
store a plurality of operating modes comprising energy delivery parameters in the memory, the plurality of operating modes comprising two or more of voltage stimulation, current stimulation, automatic temperature lesioning, manual radiofrequency lesioning, pulsed radiofrequency lesioning, or intradiscal lesioning;
detect the identifier when the connector cable is coupled to the energy generator prior to coupling of the connector cable to one medical treatment device of the plurality of medical treatment devices;
retrieve from memory, based on the detected identifier, the energy delivery parameters of a default operating mode of the plurality of operating modes, the default operating mode and at least a second operating mode of the plurality of operating modes corresponding to the detected identifier;
prior to receiving input from a user selecting an operating mode, display, on the display screen, the energy delivery parameters of the default operating mode, and displaying an option to select the at least the second operating mode; and
in response to receiving user input to select the second operating mode, display, on the display screen, the energy delivery parameters of the second operating mode,
wherein the plurality of operating modes are associated with identifiers such that different default operating modes are associated with different identifiers.

2. The energy delivery system of claim 1, wherein the energy generator is further configured to receive user input modifying the displayed energy delivery parameters and to store the modified energy delivery parameters in a profile in the memory.

3. The energy delivery system of claim 2, wherein the profile comprises an association with a selected medical treatment device.

4. The energy delivery system of claim 2, wherein the profile comprises an association with a user of the energy delivery system for a patient.

5. The energy delivery system of claim 1, wherein the identifier comprises a circuit.

6. The energy delivery system of claim 1, wherein the identifier comprises a plurality of pins on a connector of the connector cable, and the energy generator is configured to detect the identifier by determining a value corresponding to a measured voltage across the plurality of pins.

7. The energy delivery system of claim 6, wherein the energy generator further comprises:

an analog to digital converter configured to convert the measured voltage to a digital value;
a register for storing the digital value,
the digital value being retrievable by a function executing in the energy generator at an application level for use in retrieving the energy delivery parameters from the memory.

8. The energy delivery system of claim 1, wherein the energy generator is configured to detect the identifier by:
obtaining a voltage measurement at a connector of the connector cable; and
determining the identifier from the voltage measurement,
the energy generator being further configured to store the identifier, the identifier being retrievable by a function executing in the energy generator at an application level for use in retrieving the energy delivery parameters from the memory.

9. The energy delivery system of claim 1, wherein the energy delivery parameters of the default operating mode and second operating mode are displayed in screens associated with the default operating mode and second operating mode, respectively, the screens being retrievable from a graphical user interface library stored in the energy generator.

10. A method, comprising:
an energy generator storing, in memory, a plurality of operating modes comprising energy delivery parameters, the plurality of operating modes comprising two or more of voltage stimulation, current stimulation, automatic temperature lesioning, manual radiofrequency lesioning, pulsed radiofrequency lesioning, or intradiscal lesioning;
the energy generator detecting, when a connector cable is connected to the energy generator, an identifier comprised in the connector cable, the connector cable being configured to releasably couple the energy generator with a plurality of medical treatment devices;
the energy generator retrieving, from the memory, energy delivery parameters of a default operating mode of the plurality of operating modes, the default operating mode and at least a second operating mode of the plurality of operating modes corresponding to the detected identifier;
prior to receiving input from a user selecting an operating mode, the energy generator displaying, on the display screen, the energy delivery parameters of the default operating mode, and displaying an option to select the at least the second operating mode;
in response to receiving user input to select the second operating mode, the energy generator displaying, on the display screen, the energy delivery parameters of the second operating mode, wherein the plurality of operating modes are associated with identifiers such that different default operating modes are associated with different identifiers; and
the energy generator transmitting energy to a medical treatment device that is subsequently coupled to the energy generator via the connector cable in accordance with the displayed energy delivery parameters.

11. The method of claim 10, further comprising the energy generator receiving user input modifying the displayed energy delivery parameters, and storing the modified energy delivery parameters in a profile in the memory.

12. The method of claim 11, wherein the profile comprises an association with a selected medical treatment device.

13. The method of claim 11, wherein the profile comprises an association with a user of the energy delivery system for a patient.

14. The method of claim 10, wherein the identifier comprises a circuit.

15. The method of claim 10, wherein the identifier comprises a plurality of pins on a connector of the connector cable, wherein detecting the identifier comprises determining a value corresponding to a measured voltage across the plurality of pins.

16. The method of claim 15, further comprising the energy generator:
converting the measured voltage to a digital value using an analog to digital converter;
storing the digital value in a register; and
executing a function at an application level to retrieve the digital value for use in retrieving the energy delivery parameters from the memory.

17. The method of claim 10, wherein the energy generator is configured to detect the identifier by:
obtaining a voltage measurement at a connector of the connector cable; and
determining the identifier from the voltage measurement, the method further comprising the energy generator storing the identifier, the identifier being retrievable by a function executing in the energy generator at an application level for use in retrieving the energy delivery parameters from the memory.

18. The method of claim 10, wherein the energy delivery parameters of the default operating mode and second operating mode are displayed in screens associated with the default operating mode and second operating mode, respectively, the screens being retrievable from a graphical user interface library stored in the energy generator.

* * * * *